United States Patent [19]
Schnettler et al.

[11] Patent Number: 5,259,761
[45] Date of Patent: Nov. 9, 1993

[54] TOOTH VITALITY PROBE AND PROCESS

[75] Inventors: Jenifer M. Schnettler, 6831 Chillingsworth Cir., NW., Cantonand, Ohio 44718; James A. Wallace, Pittsburgh, Pa.

[73] Assignee: Jenifer M. Schnettler, Canton, Ohio

[21] Appl. No.: 579,810

[22] Filed: Sep. 10, 1990

Related U.S. Application Data

[63] Continuation-in-part of Ser. No. 562,809, Aug. 6, 1990, abandoned.

[51] Int. Cl.⁵ .......................... A61C 5/00; A61C 1/00; A61C 3/00; A61B 5/00
[52] U.S. Cl. ..................... 433/215; 433/29; 128/633
[58] Field of Search ............. 433/25, 215, 229, 29; 128/633

[56] References Cited

U.S. PATENT DOCUMENTS

| | | | |
|---|---|---|---|
| 2,685,815 | 8/1954 | Mayne | 128/633 |
| 4,184,175 | 1/1980 | Mullane | 358/93 |
| 4,479,499 | 10/1984 | Alfano | 128/665 |
| 4,564,355 | 1/1986 | Traiger et al. | 433/215 |
| 4,586,513 | 5/1986 | Hamaguri | 128/633 |
| 4,641,658 | 2/1987 | Lepper | 128/633 |
| 4,685,464 | 8/1987 | Goldberger et al. | 128/633 |
| 4,723,825 | 2/1988 | Herold | 350/96.1 |
| 4,757,381 | 7/1988 | Cooper et al. | 358/98 |
| 4,759,369 | 7/1988 | Taylor | 128/633 |
| 4,836,206 | 7/1989 | Maxwell et al. | 128/633 |
| 4,928,691 | 5/1990 | Nicolson et al. | 128/633 |

Primary Examiner—Cary E. O'Connor
Assistant Examiner—Cindy A. Cherichetti
Attorney, Agent, or Firm—Renner, Otto, Boisselle & Sklar

[57] ABSTRACT

The present invention relates to the use of pulse oximeter technology, and particularly, a pulse oximeter-like probe for diagnosing the pulpal vitality and vascular integrity of a subject tooth. The present invention does not require a reaction by the patient to pain caused by stimulation of a tooth. Thereby, the present invention is not as susceptible to false negatives or positives as were past methods for determining tooth vitality which were dependent on obtaining a neuronal response. As described herein, lack of neuronal response does not always indicate pulpal death. Both the apparatus and method of the present invention allow an immediate, objective diagnosis of tooth vitality without inducing painful stimulation.

23 Claims, 6 Drawing Sheets

TOOTH VITALITY PROBE AND PROCESS

REFERENCE TO RELATED APPLICATION

This is a continuation-in-part of copending U.S. patent application Ser. No. 07/562,809 filed on Aug. 6, 1990 now abandoned.

TECHNICAL FIELD OF THE INVENTION

The present invention relates, generally, to a non-invasive probe and process for determining the vitality of a tooth. More particularly, the present invention relates to a probe utilizing pulse oximeter technology and a method of use thereof for evaluating the vascular integrity and pulpal vitality of the tooth.

BACKGROUND OF THE INVENTION

Endodontics is a specialized branch of dentistry which deals with the study and care of the tooth pulp. Generally, the study of endodontics centers around the tooth pulp contained within the human tooth. However, endodontics may also involve the study of the teeth of other mammals or even non-mammals. Endodontics and the study and care of the tooth and tooth pulp has been an important and active field for many years.

A substantial portion of the work performed in endodontics involves the study and evaluation of the pulpal vitality and vascular integrity of the tooth. More specifically, endodontics involves evaluating the pulpal vitality and vascular integrity of a tooth in order to diagnose whether or not corrective action, such as a root canal procedure, will be necessary.

An incorrect determination that the tooth pulp is vital or healthy, commonly referred to as a false positive, could result in the delay of necessary treatment. The health of the tooth will continue to erode, often culminating in a painful root canal procedure or in the removal of the tooth. Alternatively, in the event that a healthy tooth pulp is diagnosed incorrectly as being non-vital, commonly referred to as a false negative, it could result in the unnecessary treatment of a healthy tooth and/or its removal. As a result, it is very important for those practicing endodontics to be able accurately to assess the vascular integrity and pulpal vitality of a subject tooth.

As will be described in more detail below, past and current methods practiced to determine tooth vitality have associated therewith several major drawbacks. In order to better describe such drawbacks and the use of the present invention in overcoming these drawbacks, shown in FIG. 1 is a cross-sectional view of a typical human tooth 11. More specifically, the tooth shown in FIG. 1 is a human canine tooth. However, in view of the invention as it is described below, one of ordinary skill will appreciate that such tooth could be another type of tooth, for example, a molar or incisor. Moreover, the tooth 11 need not be that of a human, but may be the tooth of some other animal.

Referring again to FIG. 1, the tooth is made up primarily of a crown section 12 and a root section 14. The crown 12 of the tooth 11 is that section which extends outwardly from the patient's gum 16, above the gum line 17. The root 14 is the portion of the tooth 11 which is located within the patient's gum 16, or below the gum line 17. The outer portion of the crown 12 is made up of a layer of enamel 18. The enamel 18 serves as a hard outer covering to the underlying layer of dentine 20 within the tooth 11.

The dentine 20 is the calcareous part of the tooth 11, below the enamel 18, which contains the pulp chamber 22 and the root canal 23. The pulp chamber 22 is the hollow area in the crown 12 of the tooth which contains the tooth pulp 24 which, as will be appreciated by those of ordinary skill, consists of nerves and blood vessels. The root canal 23 is located in the root 14 of the tooth 10, and serves as a passageway for pulp 24 to enter the pulp chamber 22.

Describing the tooth 11 in more detail, the root canal 23 originates at the base 25 of the root 14. In a healthy tooth 11, the pulp 24 enters the root canal 23 at the base 25 and occupies the entire pulp root canal 23 and the chamber 22 which extends into the crown section 12, as is shown in FIG. 1. It is through the base 25 of the root canal 23 that one or more arteries enter into the tooth 11. The arteries carry the oxygenated blood from the heart into the tooth 11. The arteries travel through the root canal 23 and form many minute capillary beds which terminate in the pulp chamber 22. Subsequently, one or more veins located within the pulp chamber 22 and root canal 23 carry the deoxygenated blood back out of the pulp chamber 22, through the root canal 23, and out through the base 25.

As is mentioned above, in a healthy tooth 11, the pulp 24 occupies the entire pulp chamber 22 and root canal 23, as is shown in FIG. 1. The pulp 24 is nourished by the blood flowing in and out of the root canal 23 into the pulp chamber 22. In turn, the pulp 24 nourishes the tooth itself. However, in an unhealthy tooth, various interruptions in the vascular integrity of the tooth 11 may occur. For example, in the event of pronounced trauma to the tooth, the flow of pulp tissue 24 from the base 25 may be interrupted. The tooth 11 will no longer be nourished by the pulp 24 contained therein. Ultimately, the pulp 24 within the tooth will die, and in the event no corrective care is provided, the tooth may eventually rot.

As another example of an unhealthy tooth, a condition referred to as calcification of the pulp chamber 22 may occur within the pulp chamber 22, thereby causing an interruption in the vascular integrity of the tooth 11. Specifically, calcification of the pulp chamber 22 relates to a condition within the tooth 11 whereby dentine deposits form at the coronal portion 26 of the pulp chamber 22, causing a reduction in the internal volume of the chamber (as is shown in phantom just below the coronal portion 26 in FIG. 1). This results in a degradation of both the amount of pulp present within the tooth 11, and of the vascular integrity of the tooth. Thus, while the pulp 24 within the tooth may remain vital or alive, in an instance such as calcification of the pulp chamber 22, there exists an interruption in the vascular integrity of the tooth 11.

Therefore, it is apparent that the pulpal vitality and the vascular integrity of the tooth 11 must be maintained in order to facilitate the longevity of the tooth. However, while the pulpal vitality and the vascular integrity of the tooth 11 are individual considerations, both are closely related. Therefore, for purposes of this invention, reference to one is intended to be equivalent to reference to the other unless otherwise noted.

For the reasons mentioned above and which are also described in more detail below, in order to provide proper preventive and remedial care to a patient's teeth, the practice of endodontics often requires the ability to evaluate properly the pulpal vitality and vascular integrity of the subject tooth. Those who practice endodontics generally have, in the past, relied on one or two non-invasive methods for evaluating the pulpal vitality and/or vascular integrity of the tooth 11. However, there are significant drawbacks to each of such past methods, as is described below.

In the past, there have been two predominant methods practiced by endodontists for evaluating or determining the pulpal vitality or vascular integrity of a tooth. One method consists of providing electrical stimulation to the subject tooth 11 and determining pulpal vitality based on the conduction of current through the enamel 18 of the tooth 11 into the nerve endings located in the pulp 24 in the pulp chamber 22 and root canal 23 within the tooth. A second method consists of a thermal test in which an extremely hot or cold substance is applied to the enamel 18 of the tooth 11, and pulpal vitality is determined based on whether thermal conduction occurs and is sensed or felt by the patient by way of the nerve endings within the tooth 11. Both methods require a reaction by the patient to pain which is not only uncomfortable but is also extremely subjective since pain tolerance may vary widely from patient to patient.

The electrical stimulation test basically involves attaching an electrode to a portion of the enamel 18 exposed on the crown 12 of the tooth. Typically, a gel toothpaste is used between the electrode and the tooth as a conductive medium. In one manner or another, the patient's body is grounded relative to the electrode. An electrical potential is then applied to the electrode relative to the ground, thereby causing a current to conduct through the tooth 11. More specifically, the current enters through the enamel 18, and is conducted through the dentine 20, through the pulp chamber 22 and out through the root canal 23. Theoretically, if the pulp 24 in the pulp chamber 22 and/or root canal 23 is vital and the nerves contained therein are healthy, the electrical current will stimulate the nerve endings in the pulp 24, resulting in a sharp pain being felt by the patient. Alternatively, if the pulp 24 is non-vital, there will be no nerve stimulation within the tooth 11, and the patient will feel no pain. An exemplary apparatus for performing the electrical stimulation test is the commercially available Model No. 2006 Vitality Scanner manufactured by Analytic Technology.

It is important to note that even if the electrical stimulation test were one hundred percent reliable, the only way to determine tooth vitality using such a method may cause sharp pain for the patient. In the event that the tooth is vital, the patient experiences extreme discomfort. Additionally, longer term ramifications must be considered for the reason that each time the electrical stimulation test is performed, the tooth is subjected to undesirable trauma.

Not only does the electrical stimulation test envelope obvious drawbacks due to patient discomfort and trauma, the electrical stimulation method also significantly produces false positives and/or negatives. For example, a false positive will occur quite often when there is a build up of liquid in the pulp chamber 22 and/or root canal 23 in place of the pulp 24. Such liquid often will build up as a result of infection, or more specifically, as a result of liquefaction necrosis. During the breakdown process, the dying pulp 24 within the tooth may introduce infection. Liquid forms within the pulp chamber 22 as a byproduct of tissue degeneration, as is known by those in the art.

Because the liquid which builds up in the pulp chamber 22 and/or root canal 23 is capable of conducting electrical current, electrical current will still be conducted through the pulp chamber 22 by way of the liquid formed therein, until the current encounters vital pulp 24 further down, in the root canal 23 for example. As a result, pain will still be introduced to the patient by the electrical stimulation of the nerve endings in the root canal 23. Therefore, in the case of liquefaction necrosis, even in the event that pain occurs using the electrical stimulation test, the pulpal vitality or vascular integrity of the tooth is not, in fact, necessarily healthy. In a substantial portion of the pulp chamber 22, in the crown 12 area for example, there may exist only the liquid which has built up. Yet, as the patient may still experience sharp pain, a false positive determination may result.

In addition, a false negative often occurs using the electrical stimulation test. For example, the tooth 11 may be traumatized to the extent that the nerve response within the tooth 11 is interrupted. Somewhat more specifically, oftentimes trauma to the tooth will induce swelling within the tooth. This swelling can interrupt the nerve response either permanently or temporarily, for up to six months or more. Therefore, in actuality, the tooth 11 and pulp 24 contained therein could be alive even though the patient experiences no pain upon the application of an electrical current. Moreover, it need not be trauma to the tooth 11 which produces an interrupted nerve response. Even though pulpal vitality and vascular integrity of the tooth remain intact, various cancers or tumors within the oral structures, for example the jaw bone, can interrupt the response of the nerves entering the tooth 11, as will be appreciated by those of ordinary skill in the art.

The thermal method mentioned above for testing pulpal vitality also has significant drawbacks in much the same manner as does the electrical stimulation test. The thermal method typically consists of either hot or cold testing. During a cold test, a coolant such as the commercially available Frigident is applied to the crown of the tooth using a cotton swab. The temperature of the coolant is such that the cold is thermally conducted through the tooth 11 until it is sensed by the nerves within the pulp chamber 22 and/or root canal 23. When using the heat test to determine pulpal vitality, an extremely hot material is applied to the tooth such that the heat is thermally conducted through the tooth 11 and felt by the nerves therein in the same manner as in the cold test.

Much like the electrical stimulation test, the thermal test is reliant upon a patient with a healthy tooth incurring significant pain in order to positively determine that the vascular integrity of the tooth is intact. Thereby, using the thermal method, a patient with a healthy tooth is likely to be subjected to sharp pain. At least in theory, only a patient with a non-vital tooth will experience no pain as the nerves in the subject tooth will be dead as a result of the deadened pulp 24.

However, for the same reasons which were detailed above, i.e. trauma, the presence of tumors, etc., the nerve response of the tooth 11 may remain deadened while the pulpal vitality and vascular integrity of the tooth remains intact. Thus, even though the tooth is healthy with respect to pulpal vitality, the nerve endings will not sense the thermal change and the thermal test will produce a false negative.

Moreover, the thermal test may also produce a false positive, especially in the situation where the patient previously has undergone significant restoration of the tooth. For example, the subject tooth may have a large filling. Oftentimes, the thermal test will result in a patient feeling pain even though the subject tooth is non-vital. In cases involving significant restoration, the heat or cold will conduct from the subject tooth to one or more neighboring teeth. Thus, the patient still will feel pain. Thus, it is extremely difficult for the patient to determine if the pain is felt by way of the nerves within the subject tooth 11, or by way of the nerves within the neighboring teeth.

In view of the foregoing, it is apparent that the methods practiced in the past for determining tooth vitality were both painful and inaccurate. As mentioned above, and as is described in greater detail below, the present invention relates to the use of oximeter technology for determining tooth vitality, and more specifically, the pulpal vitality and vascular integrity of the tooth. In the past, pulse oximeters have been known in the medical field as a non-invasive monitoring device for determining a patient's oxygen saturation and pulse rate when under intensive care or during sedation procedures. The basic operation of pulse oximeters involves light that is passed from a light emitting diode or other light source through a part of the patient's body, usually the tip of a finger, and into a photodetector or receptor. The difference in intensity of the light emitted and the light received is evaluated, typically using a microprocessor, to provide a pulse rate and oxygen saturation level measurement.

Cited as being of general interest regarding prior art pulse oximeters and the operation and use thereof, are U.S. Pat. Nos. 3,998,550, 4,266,554, 4,586,513, and 4,167,331, the entire disclosures of which are incorporated herein by reference.

Generally, a pulse oximeter measures oxygen saturation in a patient's arterial blood by evaluating the difference between the light absorption coefficient of the hemoglobin and the light absorption coefficient of the hemoglobin oxide in the patient's blood. The amount of light absorbed by the hemoglobin and the hemoglobin oxide in the blood is dependent upon the wavelength of the transmitted light. Typically, the light source emits light of two different wavelengths in order to determine the oxygen saturation of the blood in that portion of the body through which the light is transmitted. The hemoglobin oxide, or the arterial blood, and the deoxygenated hemoglobin, or the venous blood, each have an effect of the amount of absorbance which occurs with respect to the two wavelengths. It is the ratio of the absorbance of the two wavelengths that determines the percentage of oxygenation of the blood as is known in the art of oximeters. This ratio may take on many forms, as will be appreciated in view of the above mentioned patents. However, the general operation remains the same.

In view of the prior art, it is apparent that the use of the pulse oximeter for measuring the blood oxygen saturation and the pulse rate of a patient is well known. However, until the present invention, there was no accurate, non-invasive device or process for determining the vitality of a human tooth utilizing a pulse oximeter. Instead, for years endodontists have had to rely on such past methods as the above described electrical stimulation test, and the hot and cold thermal tests. As a result, patients have been forced to suffer pain which must be inflicted in order to determine, although inaccurately at times, the pulpal vitality and vascular integrity of the subject tooth.

In view of the foregoing shortcomings of previous methods and techniques for determining tooth vitality, there has existed a strong, long felt need for a tooth vitality probe and process for determining tooth vitality in a painless, non-invasive, accurate manner.

SUMMARY OF THE INVENTION

The present invention relates to the use of pulse oximeter technology, and particularly, a pulse oximeter-like probe for diagnosing the pulpal vitality and vascular integrity of a subject tooth. The present invention does not require a reaction by the patient to pain caused by stimulation of a tooth. Thereby, the present invention is not as susceptible to false negatives or positives as were past methods for determining tooth vitality which were dependent on obtaining a neuronal response. As described herein, lack of neuronal response does not always indicate pulpal death. Both the apparatus and method of the present invention allow an immediate, objective diagnosis of tooth vitality without inducing painful stimulation.

Therefore, in accordance with one aspect of the present invention, a non-invasive photoelectric probe is provided for determining the vitality of a tooth, the probe including a light source for transmitting light through at least a portion of the pulp chamber of the tooth, a detector for detecting the transmitted light after it passes through the pulp chamber, the detector providing an output signal which is indicative of the absorption of the light which occurs after being transmitted through the portion of the tooth, a processor for converting the output signal into an oxygen saturation measurement of the blood contained in the pulp chamber, and means for indicating tooth vitality based on the measurement.

In accordance with another aspect of the present invention, a sensor is provided for use in the non-invasive diagnosis of the vitality of a tooth, the sensor including a light source for providing light to be transmitted through at least a portion of the pulp chamber in the tooth, a detector for detecting at least part of the transmitted light and for providing a output signal indicative of the amount of the light absorbed by the blood within the pulp chamber, a sensor body for maintaining the light source and detector in fixed, facing relation on generally opposite sides of the tooth so as to provide a source to detector path which intersects the pulp chamber, and an engagement mechanism for engaging the light source and detector against the respective sides of the tooth.

In yet another aspect of the present invention, a non-invasive diagnostic method for determining tooth vitality is provided, the method comprising the steps of transmitting light through at least a portion of the pulp chamber within the tooth, detecting at least a portion of the transmitted light, and evaluating the intensity of the received light in order to provide an indicia for determining the pulpal vitality of the tooth.

In accordance with another aspect of the present invention, a non-invasive method for determining the vitality of a tooth is provided, wherein the method includes the steps of non-invasively measuring the blood oxygen saturation level of blood contained within the pulp chamber of the tooth, and comparing the measurement to a predetermined criteria in order to determine the vitality of the tooth.

The invention is described in detail below with respect to the preferred embodiment. Accordingly, although a preferred embodiment is described, the invention is to be limited only by the scope of the claims hereof and the equivalents thereof.

To the accomplishment of the foregoing and related ends, the invention, then, comprises the features hereinafter fully described in the specification and particularly pointed out in the claims, the following description and the annexed drawings setting forth in detail certain illustrative embodiments of the invention, these being indicative, however, of but several of the various ways in which the principles of the invention may be employed.

DETAILED DESCRIPTION OF THE PREFERRED EMBODIMENT

Figure 2:
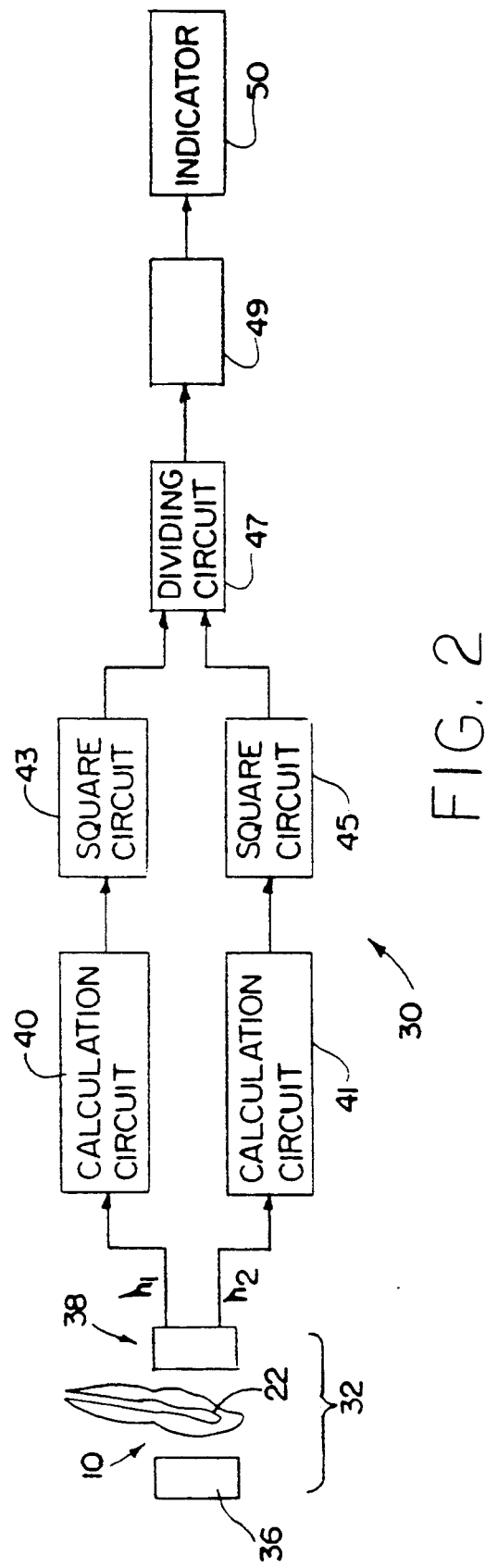
FIG. 2 is a block diagram of the preferred embodiment of the present invention.

Referring now to the drawings, and more particularly to FIG. 2, a tooth vitality probe 30 in accordance with the present invention is shown. The probe 30 includes a probe sensor 32 which is to be attached in fixed relation the subject tooth 11 which is being measured for vitality. The probe sensor 32 includes a light source 36 and a photodetector 38. The light source 32, which may consist of a light emitting diode (LED) or the like, emits light of two different wavelengths, such wavelengths being determined as set forth below. While a single LED which emits both wavelengths is utilized in the preferred embodiment, two separate LEDs (one for each wavelength) similarly may be employed.

The photodetector 38 is designed to detect both wavelengths of the transmitted light once the light transmitted through the crown portion 12 of the tooth 11 and has come in contact with the pulp chamber 22 and the pulp 24 contained therein. If the tooth is vital, the transmitted light will come into contact with the arterial blood contained within the pulp 24. In the event the tooth is non-vital, at least to the extent of containing no pulp 24 or arterial blood in the pulp chamber 22, the light from the source 36 will pass through the tooth 11 to the detector 38 uninterrupted by arterial blood flow.

The remaining components of the probe 30, namely the calculation circuits 40 and 41, the square circuits 43 and 45, the dividing circuit 47, the linear function circuit 49 and the indicator 50, are made in accordance with, and function according to known pulse oximeter techniques. Specifically, the embodiment shown in FIG. 2 incorporates the pulse oximeter which is fully described in the U.S. Pat. No. 4,586,513 mentioned above, and which is summarized below. However, while the present invention is described herein as incorporating the specific pulse oximeter technology disclosed in the '513 patent, the oximeter is but one of many types of pulse oximeters which could similarly function as a part of the present invention.

Accordingly, any reference to the oximeter described in the '513 patent is for the purpose of providing adequate disclosure for a single embodiment, and is not intended to limit the intended scope of the present invention. Other embodiments perform equally as well. For example, as is described in greater detail below, the inventors have achieved satisfactory results by using the probe sensor 32 described herein in conjunction with the commercially available pulse oximeter unit manufactured by Novametrix as Model No. 500.

The photodetector 38 shown in FIG. 2 is capable of detecting light at the two wavelengths of interest, specifically $\lambda_1$ and $\lambda_2$. It is known that the hemoglobin and hemoglobin oxide in a patient's blood each absorb light having a wavelength in the infrared region to approximately the same degree. However, the hemoglobin has a light absorption coefficient for light in the visible region which is substantially different than that of the hemoglobin oxide. Thus, by comparing the relative absorption characteristics of light transmitted through a patient's blood, and more particularly, the blood contained within the pulp chamber 22, the probe 30 is capable of measuring a patient's blood oxygen saturation level and pulse rate.

However, the probe 30 also serves a much more important function. Specifically, the probe 30 provides a painless, accurate, non-invasive, indication of the pulpal vitality and vascular integrity of the tooth 11.

More specifically, the probe sensor 32, as is described above, transmits light of two different wavelengths from the source 36 along a path which intersects at least a portion of the pulp chamber 22 within the tooth 11. The source 36 and detector 38 are aligned on opposite sides of the tooth 11 along the crown 12 such that the light is transmitted from the source 36 directly towards the center of the tooth, through the pulp chamber 22, and towards the detector 38 where the light is then detected. Typically, the first wavelength of light $\lambda_1$ is in the infrared region, and is absorbed to the same degree whether the blood be hemoglobin, hemoglobin oxide, or a combination thereof. The second wavelength of light $\lambda_2$ is typically in the visible region, but most importantly, is selected such that it is absorbed more or less readily depending on the amount of hemoglobin oxide in relation to hemoglobin which is present in the blood within the pulp chamber 22.

The photodetector 38, as was mentioned above, detects the light transmitted through a patient's tooth 11, and particularly the blood within the pulp chamber 22.

Therefore, both wavelengths of light which are not absorbed within the tooth, and more importantly, by the blood within the pulp chamber 22, are detected and converted into electrical signals by the photodetector 38. The electrical signals are representative of the intensity of the light detected for each wavelength, and the electrical signals are further processed and monitored within the oximeter internal circuitry to provide an indication of the patient's blood oxygen saturation.

Generally, the electrical signals labeled $\lambda_1$ and $\lambda_2$ in FIG. 2 each include an alternating current (AC) component and a direct current (DC) component as is known by those of ordinary skill in the field of oximeters. The AC component relates to the absorption caused by the pulsating blood in the arteries, and the DC component relates to absorption by the general structure of the tooth.

As a result, the probe 30 is capable of detecting the presence of a pulse in the blood located within the pulp chamber 22 by way of detecting the presence of an AC component from the sensor 32. The pulse is indicative of an interchange of arterial and venous blood occurring within the pulp chamber. It will be appreciated that such an interchange will not occur in a non-vital tooth, as the pulsating arterial blood will not be present in the pulp chamber 22. In the event the AC component from the sensor 32 is absent or negligible, those of ordinary skill in the art of oximeters will recognize that this indicates the absence of a pulse.

In the exemplary embodiment shown in FIG. 2, the calculation circuits 40 and 41 calculate information representative of the amplitude of the AC component relative to the DC component, which provides a reference level with respect to the two wavelengths, $\lambda_1$ and $\lambda_2$, respectively, as is described more fully in U.S. Pat. No. 4,586,513. The outputs from the calculation circuits 40 and 41 are squared, subsequently, by the pair of square circuits 43 and 45, respectively. The dividing circuit 47 is for obtaining the above-mentioned ratio between the outputs from the pair of square circuits 43 and 45. The output from the dividing circuit 47, which corresponds to the square of the ratio between the outputs of the pair of first calculation circuits 40 and 41, is transmitted to a linear function circuit 49 where it is multiplied by a first constant and added to a second constant. The result of the calculation by the linear function circuit 49 is representative of the oxygen saturation of the blood located in the pulp chamber 22 and in the path of the transmitted light. The blood oxygen saturation level then can be displayed by an indicator 50 such as a meter or digital display circuit.

Therefore, the probe 30 is capable of measuring the blood oxygen saturation level of the blood within the pulp chamber 22, and is also capable of detecting the pulse rate of the patient. More specifically, a pulsatile AC component is detected by the sensor 32 as a result of the pulsatile blood flow within the arteries in the pulp chamber 22, as mentioned above. This indicates an interchange of arterial and venous blood within the pulp chamber 22, and the relative extent of such interchange is then utilized to calculate the blood oxygen saturation level.

Thus, the vitality of a subject tooth of a patient may be tested using the probe 30. The probe sensor 32 is engaged with the tooth 11 and an oxygen saturation level is determined. The oxygen saturation level then may be compared against a predetermined criteria, and an assessment of tooth vitality may be made. Such a comparison may be performed automatically within the probe 30 circuitry, or by the operator. As an example of such a criteria, it has been found that a vital tooth generally will produce an oxygen saturation level within the range of 85 to 100 percent. Thus, if the oxygen saturation reading is within the predetermined range representing positive tooth vitality, the tooth vitality test will prove positive, indicating that the tooth is vital.

Measurement of a very low oxygen saturation level would be indicative of a non-vital tooth. More specifically, the operator would know that the pulp 24 in the tooth 11 was dead or substantially dead, or that the tooth had incurred an interruption in vascular integrity. Again, the oxygen saturation reading preferably would be compared against a predetermined criteria which would indicate non-vitality. For example, the probe 30 circuitry could be configured such that if the oxygen saturation level were in the range of 0 to 25 percent, the probe would indicate a non-vital tooth.

The present invention would not be subject to error under the circumstances described above which, as was explained, caused a false positive to occur when using past methods for testing tooth vitality. Furthermore, the present invention is not subject to producing the same false negatives with respect to tooth vitality as were the methods in the past.

Should the oxygen saturation level obtained from the tooth 11 result in what may be referred to as an intermediate level, for example in the range of 25 to 85 percent, this information can be utilized for further analysis as to the specific stage of the pathologic process of the pulp 24.

As an alternative method or criteria for determining tooth vitality, the present invention includes the aspect of simply detecting the presence or absence of a pulse in the tooth 11. As is explained above, the probe sensor 32 is capable of detecting a pulse in the arterial blood flow by virtue of the presence of an AC component in the signals representative of wavelengths $\lambda_1$ and $\lambda_2$. Those of ordinary skill in the art will appreciate that the absence of a pulse in the tooth 11 indicates non-vitality. The absence of the pulse may be non-invasively and objectively determined based on the absence of the AC component. Alternatively, the presence of the AC component, and therefore, the presence of a pulse, would indicate tooth vitality since arterial blood is present in the pulp chamber 22. The probe 30 circuitry thus would be configured to indicate the presence or absence of the AC component, preferably by way of the indicator 50.

Yet another method or criteria for non-invasively determining tooth vitality in accordance with the present invention involves the detection of an interchange of arterial and venous blood within the pulp chamber 22. As is explained above, the probe sensor 32 is capable of detecting an interchange of arterial and venous blood based on the presence of a pulse and/or based on the detection of a relative variation in absorbance of the transmitted light due to the exchange of hemoglobin oxide and hemoglobin as is known to those of ordinary skill in the field of oximeter technology. Thus, a criteria may be utilized wherein if the probe 30 detects an interchange of arterial and venous blood, the tooth is considered to be vital. In the event no interchange of arterial and venous blood is detected within the tooth, the tooth is considered non-vital, and endodontic treatment should result. Again, the probe 30 circuitry could be configured, as will be appreciated by those of ordinary skill, to indicate that an interchange of blood is or is not occurring during a measurement. Such indication preferably would occur at the indicator 50.

The present invention is discussed primarily in the context of a pulse oximeter for measuring the oxygen saturation level of the blood within the tooth 11. However, in accordance with the criteria set forth above, it is within the scope of the present invention to utilize any other type of machine capable of non-invasively detecting the presence or absence of a pulse within the tooth, and/or capable of non-invasively detecting the interchange of arterial and venous blood flow within the tooth. Accordingly, while the preferred embodiment is described as incorporating pulse oximeter technology, it is not intended that the present invention be so limited.

Figure 1:
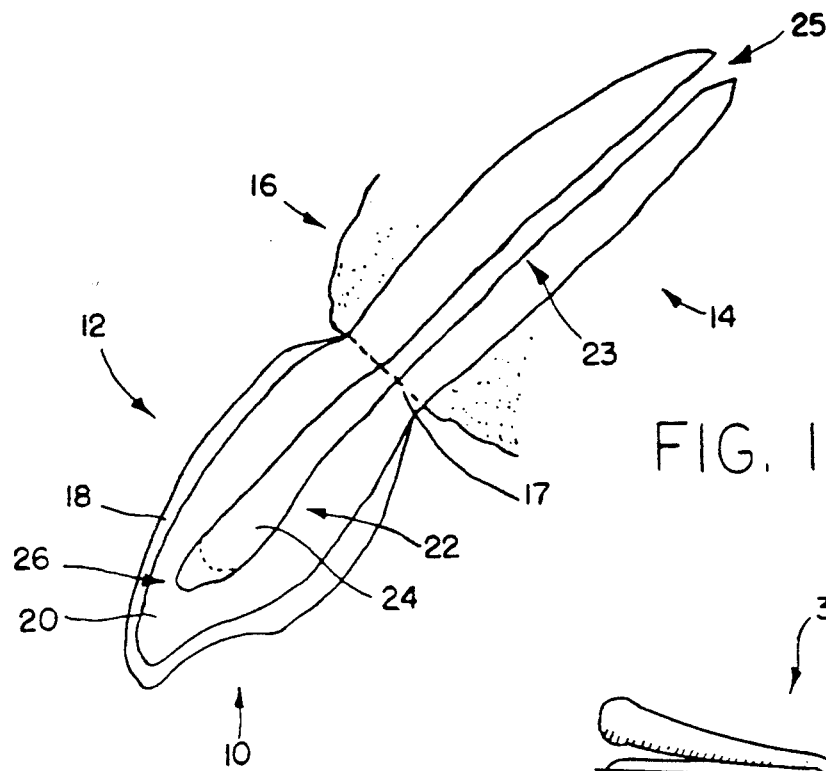
FIG. 1 is a cross-sectional view of a human canine tooth.
Figure 4:
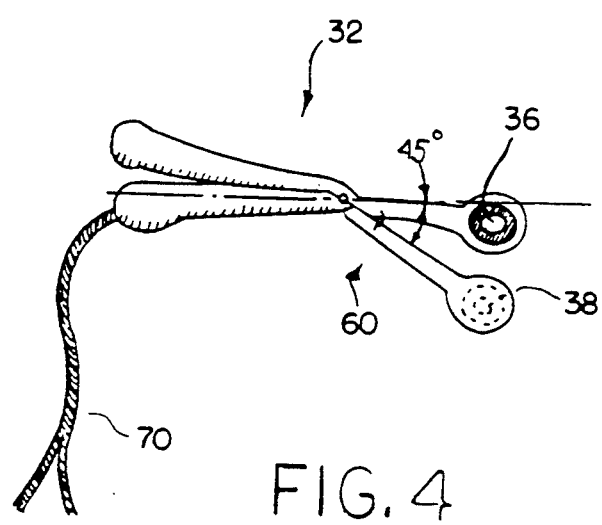
FIGS. 3 and 4 are top and side perspective views, respectively, showing the preferred embodiment of the probe sensor which engages the tooth in accordance with the present invention.
Figure 3:
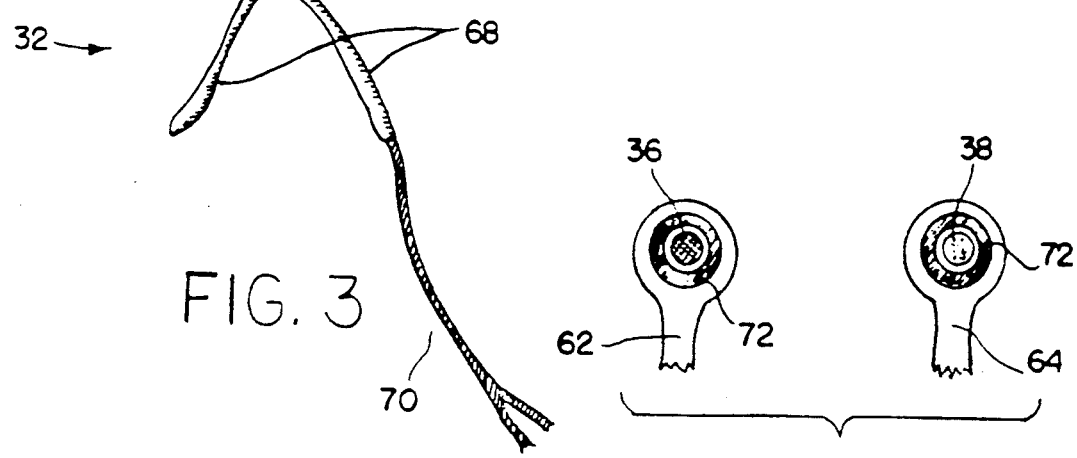

Referring now to FIGS. 3 and 4, the preferred embodiment of the probe sensor 32 is shown. As in indicated, the sensor 32 includes the light source 36 and photodetector 38. The sensor housing 60 preferably is shaped somewhat in the form of a clothes pin. The sensor 32 has rigid arm members 62 and 64 upon which the light source 36 and detector 38, respectively, are fixedly attached in facing relation. In the preferred embodiment, the rigid arm members 6 and 64 are sufficiently thin so as to facilitate the insertion of the light source 36 and detector 38 below the gum line 17 (FIG. 7) when desired.

The sensor housing 60 also includes a biasing member 66, such as a small spring, which exerts an inwardly directed force on both rigid arm members such that the light source 36 and detector 38 are drawn continuously towards each other. Thus, when the light source 36 and detector 38 are positioned on opposite sides of the subject tooth 11, the effect of the bias member 66 will be such that the sensor 32 will remain fixedly attached to the tooth 11 due to the gripping action of the sensor 32.

In order to facilitate the application and removal of the sensor 32 from the tooth 11, the sensor housing 60 includes tabbed end sections 68. When pinched together, the tabbed end sections 68 counteract the force of the bias member 66 such that the light source 36 and detector 38 are separated. Once the light source 36 and detector 38 are separated as such, the probe 32 may be attached to or removed from the tooth 11 quite easily.

In the preferred embodiment, the rigid arm members 62 and 64 are angled with respect to the tabbed end sections 68 to account for the alignment of the various teeth and to facilitate access to the rear teeth such as the molars. Most preferably, the angle between the tabbed ends and the arm sections is the forty-five degree contra-angle which is standard with endodontist's tools. The sensor 32 also includes wire leads 70. The wires 70 are connected to the light source 36 and the detector 38, and the other ends of the wires 70 are connected the appropriate inputs in the oximeter probe 30, as is known.

Figure 5:
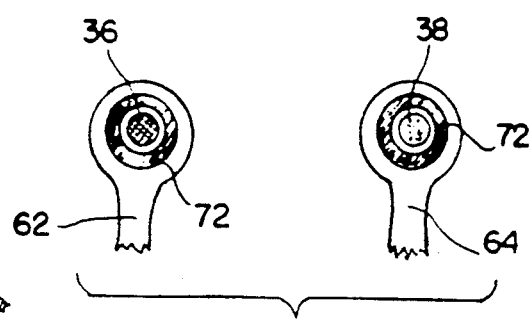
FIG. 5 is a perspective view, in partial cutaway, of the light source and photodetector in the probe sensor of FIGS. 3 and 4.

FIG. 5 shows a partial plan view of the light source 36 and detector 38, particularly as each element would face the respective sides of the subject tooth 11. Surrounding the light source 36 on the arm 62 is a small, opaque, rubber o-ring 72, or the like, which serves to form a compliant seal between the light source 36 and the side of the tooth 11 to which it is affixed. Likewise, the detector 38 is surrounded by a similar o-ring 72. Rarely will a tooth be substantially flat on both sides. Therefore, in the preferred embodiment, the sensor 32 includes the o-ring 72, or the like, which concentrically surrounds the source 36 and detector 38 as shown in FIG. 5. Because the o-rings 72 themselves are compliant, the source 36 and the detector 38 will remain in optical facing relation regardless of the type, or more particularly, the shape of the subject tooth 11.

However, not only do the o-rings 72 facilitate keeping the source 36 and detector 38 in proper optical alignment, but the o-rings 72 also help to prevent the transmission of light in a direction not along the source-to-detector path. Moreover, the o-ring 72 surrounding the detector will assist in preventing the detector 38 from detecting light not along the source-to-detector path.

Figure 6:
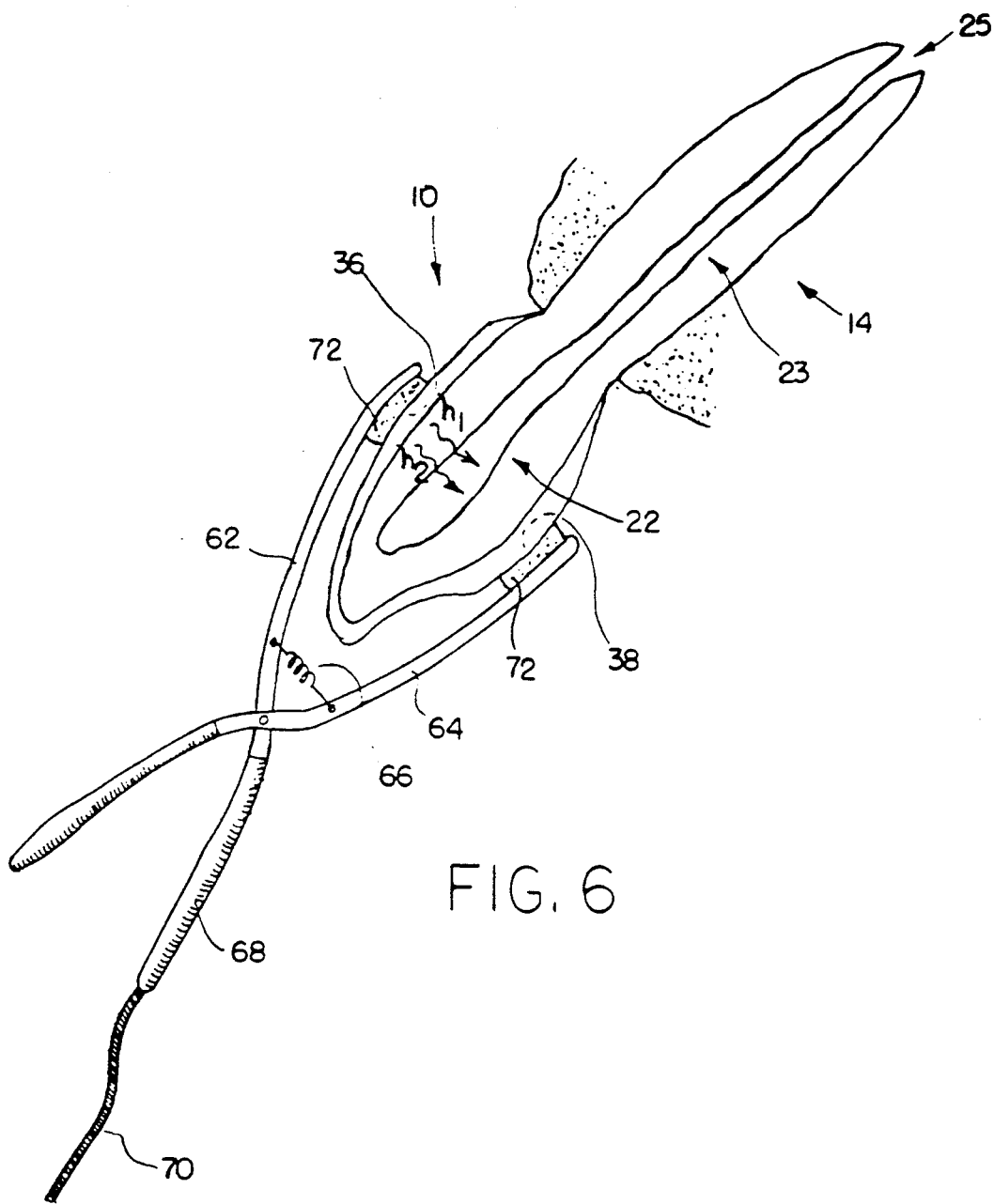
FIG. 6 is a cross-sectional view of the tooth of FIG. 1, further including a perspective view of the probe sensor of FIGS. 3 and 4 in engaged relation with the tooth.

Specifically, the light emitted from the source 36 will be isolated in a cavity formed by the o-ring 72 which is in pressed engagement with the side of the tooth 11 as is shown in FIG. 6. Thereby, the light is transmitted from the light source 36 only in the direction which is through the tooth 11 and towards the detector 38. The opaque nature of the o-ring prevents light from escaping out the sides of the cavity. In much the same manner, the o-ring surrounding the detector 38 acts to isolate the detector 38 and contain the light which is transmitted through the tooth 11. As a result, a substantial portion of both wavelengths of light is transmitted through the pulp chamber 22 and received by the detector 38 in order to provide a more accurate reading.

Figure 7:
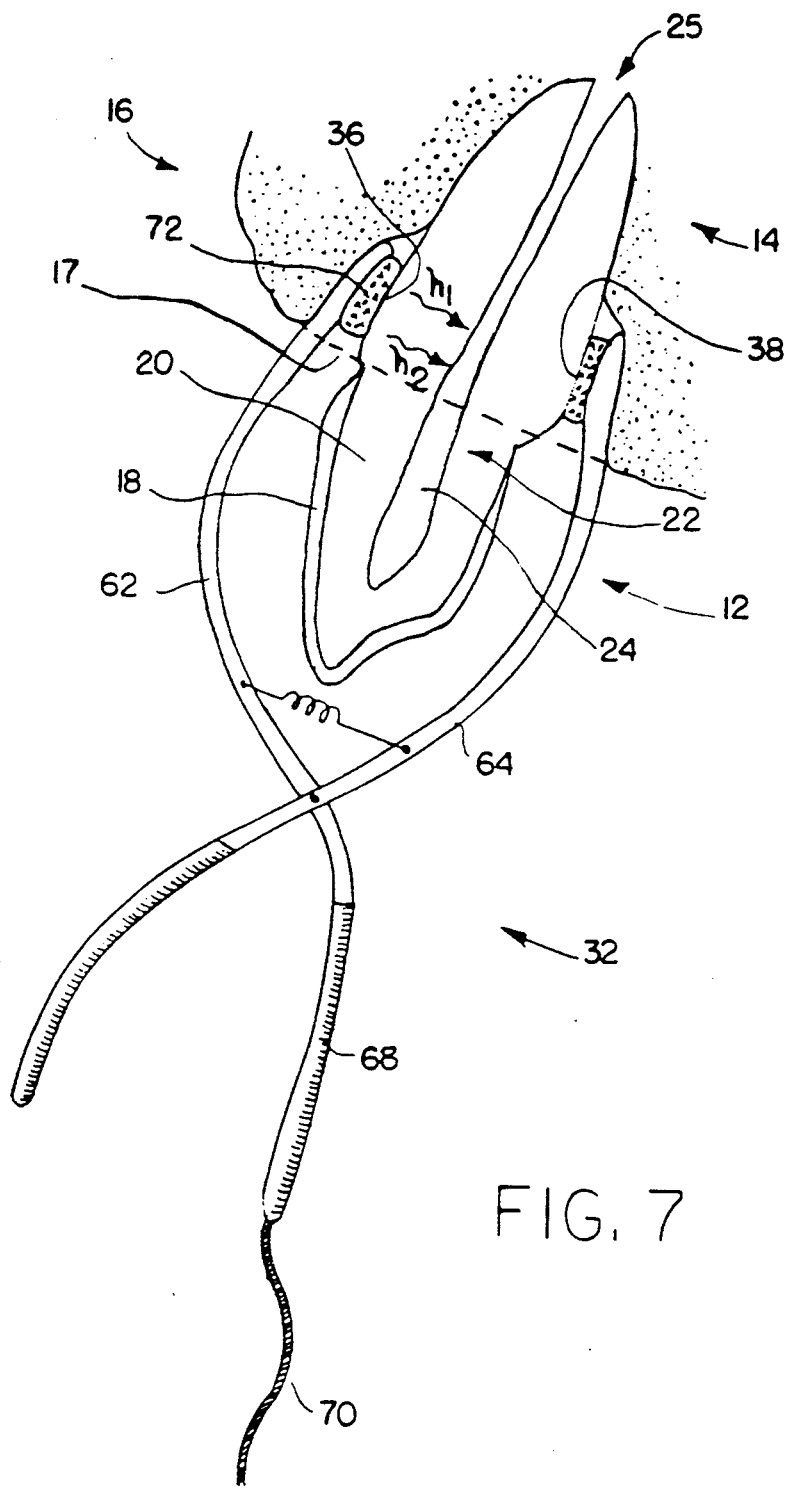
FIG. 7 is a cross-sectional view of the tooth of FIGS. 1 and 6, including a perspective view of the probe sensor in engaged relation with the tooth, below the gum line, in accordance with another feature of the present invention.

FIG. 7 exemplifies how the sensor 32 is equally suited for attaching to a tooth just below the gum line 17. More specifically, FIG. 7 shows the sensor light source 36 and detector 38 engaged with the tooth 11 below the gum line 17, and as a result, the source-to-detector path taken by the light will intersect the root canal 23 in the root section 14 of the tooth rather than the pulp chamber 22 in the crown 12.

Operation of the probe 30 and the probe sensor 32 is identical whether the sensor 32 is positioned above or below the gum line 17. The only difference is that with the sensor 32 positioned below the gum line 17, tooth vitality is determined based on the detected properties of the pulp contained within the root canal 23 instead of the pulp chamber 22.

Various situations may arise where the positioning of the sensor 32 below the gum line 17 is desirable. For example, in cases of severe trauma where the crown section 12 of the tooth may be lost, and the operator still may wish to determine the vitality of the tooth 11 with respect to the root section 14. As another example, the presence of a porcelain fused to metal, or an all metal crown, may prohibit the sensor 32 from obtaining a vitality measurement in the event the sensor 32 is positioned about the crown 12 (as described in more detail below). By placing the sensor 32 below the gum line 17, the probe 30 may still determine the vitality of the tooth by measuring the oxygen saturation level of the blood contained within the root canal 23 in the root 14 of the tooth.

Another example of a situation conducive to positioning the sensor 32 below the gum line involves significant recession of the pulp chamber 22. More specifically, in some circumstances, there is substantial calcification within the pulp chamber 22, which causes the pulp chamber 22 to recede towards the root canal 23. While such calcification may prohibit an oxygen saturation measurement at the crown 12, a reading still may be obtained based on the blood contained in the pulp 24 within the root canal 23.

Therefore, the present invention allows the operator to assess vitality of the tooth based on a measurement at the crown 12, at the root 14, or both. A positive vitality reading at the crown 12 indicates that the entire tooth 11 is vital. A negative vitality reading at the crown, combined with a positive vitality reading at the root section 14, would indicate a healthy root, but that the pulp chamber 22 has receded and that endodontic treatment may be necessary at least with respect to the crown 12. A negative vitality reading at both the crown 12 and root 14 would indicate a dead or substantially deadened tooth 11.

Figure 8:
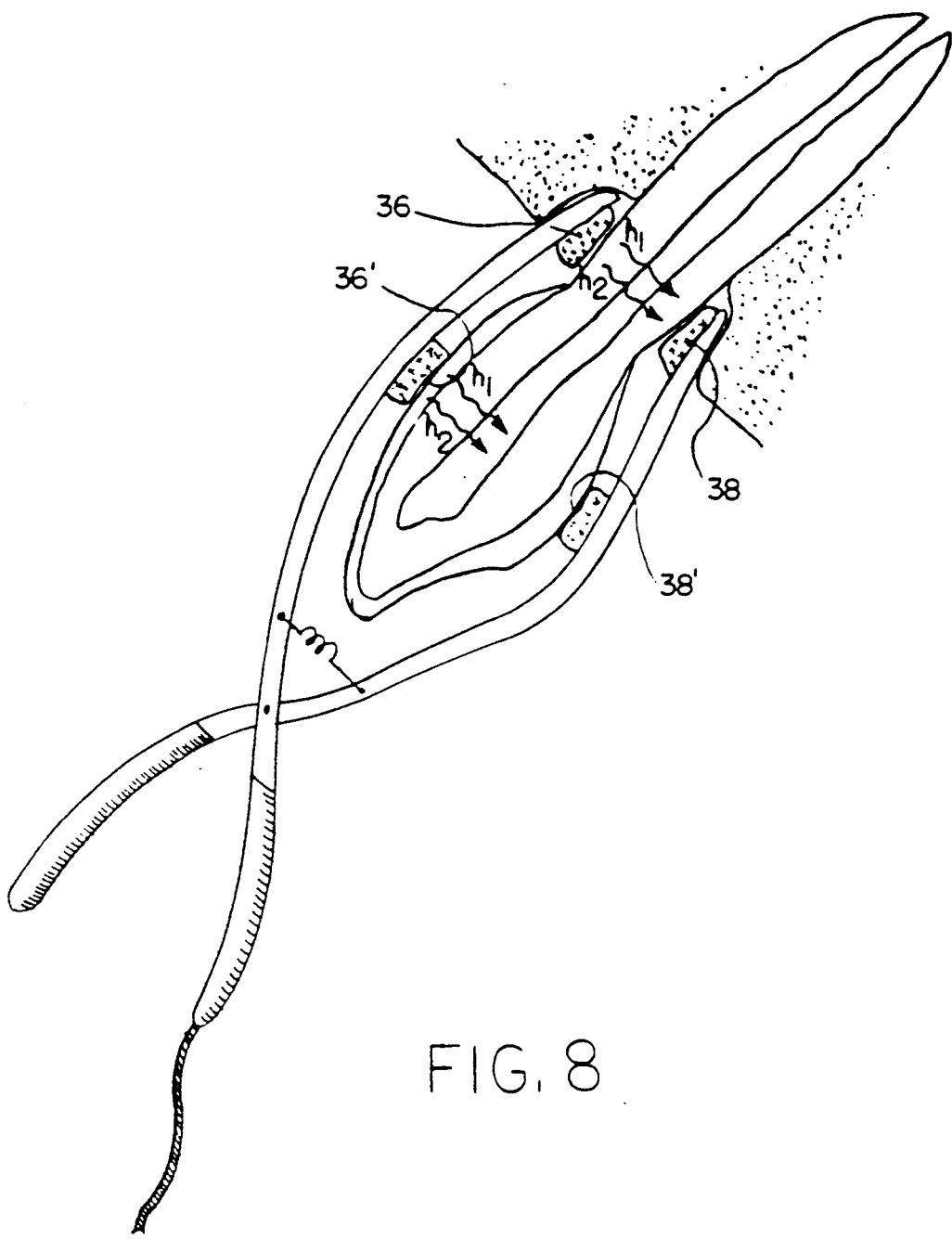
FIG. 8 is a perspective view of an alternate embodiment of the probe sensor of the present invention.

Moreover, the probe sensor 32 may be configured such that there are two or more sets of light sources 36, 36' and photodetectors 38, 38' positioned adjacent to one another along the support arms. As is shown in FIG. 8, one light source and detector set 36 and 38 may be engaged below the gum line against the tooth, and the other set 36' and 38' may be engaged across the crown 12. Thus, the entire tooth may be tested at one time.

Figure 9:
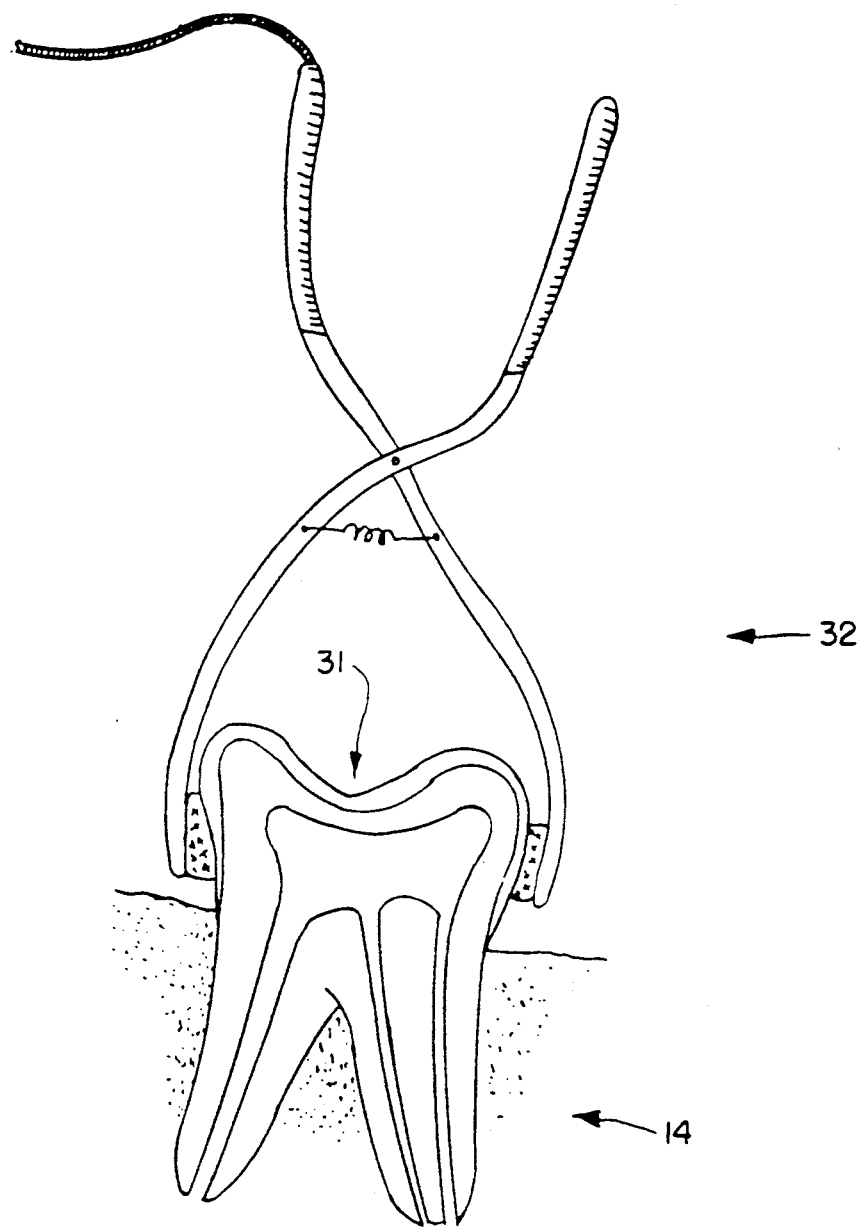
FIG. 9 is a cross-sectional view of a human molar tooth showing the probe of FIGS. 3 and 4 in engagement therewith in accordance with the present invention.

Referring briefly to FIG. 9, the sensor 32 is shown in engagement with a molar 31 rather than a canine tooth 11. FIG. 8 shows that the sensor 32 may be attached to a variety of teeth.

FIGS. 3-8 show one embodiment of the pulse sensor 32 of the present invention. However, it shall be apparent that several other embodiments are possible without departing from the intended scope of the invention. For example, the sensor 32 may contain a light source 36 and detector 38 which are positioned on sensor pad supports that are made of a thin, soft, resilient material which conforms to the crown or exposed portion of the tooth 11 with which they are engaged in contact. As another example, rather than utilizing a clothes-pin like, rigid arm type housing as shown in FIGS. 3-8, the sensor 32 may be made of a flat strip of flexible material which supports both the light source 36 and the detector 38. The flexible material would preferably have an adhesive layer on one side for adhering to the surface or enamel of the tooth. Examples of probes similar to these different embodiments, and as utilized with pulse oximeters in the conventional context of measuring a patient's oxygen saturation and pulse rate, are described in U.S. Pat. Nos. 4,685,464 and 4,830,014. The entire disclosure of each of these patents is incorporated herein by reference.

However, regardless of the specific design of the sensor housing 60, the critical feature is that the sensor 32 be capable of being properly positioned such that light is transmitted and detected through the pulp chamber 22. Moreover, it is important that the sensor remain fixed in position with respect to the tooth during the operation of the probe 30 in order to avoid errors due to motion artifacts.

Experimental Results

Recent experiments performed by the inventors have evidenced the fact that the present invention is useful as a non-invasive, accurate, and most importantly, painless apparatus and process for determining tooth vitality. During these experiments, forty-nine human subjects were tested in accordance with the present invention for vitality of one of their maxillary central incisors. For comparison purposes, pulse rate and oxygen saturation levels were obtained for each subject. For these measurements, the pulse rate and oxygen saturation for each subject were measured at the subject's finger using a conventional sensor.

In order to investigate the vitality of each subject's tooth, the Novametrix pulse oximeter Model No. 500 was equipped with a probe sensor 32 in accordance with the present invention. In addition, the cold test using Frigident was used on the subjects, as was the electrical stimulation test using the above-mentioned Analytic Technology tester.

As is known, the numeric values obtained from a pulse oximeter are specific to each subject. Typically, these values vary within a range predefined as being normal, and the pulse oximeter allowed the operator to set parameters of upper and lower tolerances. For this particular experiment, the normal parameters for pulse rate (resting) were defined at between 50 and 120 beats per minute. The normal parameters for oxygen saturation were defined at between 86 and 100 percent.

With respect the oxygen saturation and pulse rate measurements as obtained from the subject's fingers, all fortynine of the subjects tested within the normal limits. The average pulse rate was 72 beats per minute, and the average oxygen saturation reading was 97 percent.

With respect to the testing of each subjects tooth, the probes sensor 32 was attached to the tooth in accordance with the description provided above. Readings representing the oxygen saturation of the blood within the tooth were taken for each subject using the Novametrix pulse oximeter. The basic premise was that if the tooth were vital, an oxygen saturation level would be obtained which was comparable to that obtained from the subject's finger. Alternatively, if the subject's tooth were non-vital, an oxygen saturation measurement substantially equal to zero would result.

However, it is noted that if the tooth to be tested had a full crown restoration, which is impermeable to light, an inaccurate probe reading would likely result. While full porcelain crowns or veneers permit light to transmit through the tooth to register vitality status, full porcelain crowns fused to metal prohibit the passage of light through the crown. Yet, the presence of such restoration would be plainly evident, and the endodontist would know that a vitality reading across the root 14, as described above, or an alternate method for determining tooth vitality must be used.

Upon completion of the experiments, it was determined that if the measured tooth were vital, the values recorded for the subject's finger versus that for the tooth remained within a predictable range of one another. Typically, a vital tooth registered an oxygen saturation reading within 5 percent of that registered by the finger. The results of the experiment showed that the average oxygen saturation reading of the vital teeth was 94 percent as compared to the 97 percent average for the fingers. In the event that the subject's tooth was non-vital, an abnormally low oxygen saturation reading resulted using the probe 30, indicating deadened pulp and/or interrupted vascular integrity within the tooth.

It is believed that the difference between the oxygen saturation reading measured at the finger and that measured at a vital tooth (approximately 3% on the average) was due to the diffraction of the light travelling through the tooth. It is believed that the organic matrix making up the tooth, primarily one of calcium salt, causes such diffraction. As with other pulse oximeters, the probe sensor 32 may be calibrated to account for such error, as is known in the oximeter field.

As for the details of the experimental results, five of the tested teeth had been previously endodontically treated. These five teeth were assigned to Group I. The forty-four teeth with vitality unknown were assigned to Group II. The probe 30 values for both the finger and central incisor were recorded for all forty-nine subjects, and a positive or negative response to the cold and electric tests was determined.

The forty-four teeth in Group II all exhibited positive responses to the cold and electrical stimulation tests. The five teeth in Group I responded negatively to both tests. Values for the finger readings from the oximeter 30 the conventional finger tip sensor were recorded, and no individuals exhibited readings out of the normal parameters for pulse rate and oxygen saturation.

Using the probe 30 of the present invention, the forty-four teeth in Group II all exhibited positive responses by providing oxygen saturation readings substantially equivalent to the recorded finger reading. With respect to Group I, the probe 30 registered an oxygen saturation reading of almost zero percent.

In view of the above, it may be seen that the present invention is capable of providing an accurate diagnosis of the tooth vitality. The apparatus and method are completely non-invasive, and the invention demonstrates superior patient acceptance since the present invention does not induce pain to discern vitality.

While the preferred embodiment of the present invention has been specifically described herein, it will be apparent that numerous modifications may be made thereto without departing from the scope of the invention as defined in the appended claims. For example, the invention as described herein utilizes a two wavelength oximeter. As is known in the field of oximetry, three and four wavelength oximeters also are available, usually in the event that there is a need for increased accuracy. Moreover, the present invention is described as utilizing a transmissive type pulse oximeter. However, it will be apparent to those of ordinary skill that a reflectance type pulse oximeter will work equally as well. In addition, the invention does not require that it be a pulse oximeter which measures the oxygen saturation of the blood contained in the pulp chamber 22. Rather, it may be some other type of oximeter which is capable of non-invasively measuring the oxygen saturation of the blood within the pulp chamber.

What is claimed is:

1. An apparatus for non-invasively determining the vitality of a tooth, said apparatus comprising:
   means for obtaining a blood oxygen saturation measurement of blood contained in a portion of at least one of the pulp chamber or root canal of said tooth, said means for obtaining comprising means for detecting a pulsatile component in said blood and means for determining said oxygen saturation measurement based on said pulsatile component; and
   means for comparing said oxygen saturation measurement to a predetermined criteria in order to determine said vitality of said tooth.

2. The apparatus of claim 1, wherein said predetermined criteria comprises two separate ranges, a first range consisting of values of oxygen saturation predetermined to represent a vital tooth, and a second range of values predetermined to represent a non-vital tooth.

3. The apparatus of claim 2, wherein said first range comprises the values of 85 to 100 percent blood oxygen saturation, and said second range comprises the values of 0 to 84 percent blood oxygen saturation.

4. The apparatus of claim 2, wherein said predetermined criteria comprises a third range including values predetermined to represent various intermediate pathological stages of said tooth, said stages being between vital and non-vital.

5. The apparatus of claim 4, wherein said first range comprises the values of 85 to 100 percent blood oxygen saturation, said second range comprises the values of 0 to 10 percent oxygen saturation, and said third range comprises the values of 11 to 84 percent oxygen saturation.

6. The apparatus of claim 1, wherein said means for obtaining a blood oxygen saturation measurement comprises:
   a photoelectric sensor, said sensor comprising:
      light source means for providing light to be transmitted through said portion of said tooth;
      detector means for receiving at least part of said transmitted light and for producing an output signal which is indicative of the degree of absorption of said received light due to said blood within said portion of said tooth; and
      a sensor body for maintaining said light source and detector means in fixed, facing relation on generally opposite sides of said tooth so as to provide a source to detector path which intersects said portion of said tooth; and
   processing means for converting said output signal into said oxygen saturation measurement.

7. The apparatus of claim 6, wherein said light from said light source means comprises light of first and second wavelengths, said first wavelength being a wavelength for which hemoglobin and hemoglobin oxide in a patient's blood each have approximately the same light absorption coefficient, and said second wavelength being a wavelength for which said hemoglobin and hemoglobin oxide have differing light absorption coefficients.

8. The apparatus of claim 7, wherein said first wavelength is in the infrared region of the light spectrum, and said second wavelength is in the visible region of the light spectrum.

9. An apparatus for non-invasively determining the vitality of a tooth, said apparatus comprising:
   means for detecting the presence of a pulse in said tooth; and
   means for indicating that the tooth is vital in the event a pulse is detected, and for indicating that the tooth is non-vital in the event said pulse is not detected.

10. The apparatus of claim 9, wherein said means for detecting the presence of a pulse comprises a photoelectric sensor, and wherein said sensor comprises:
   light source means for providing light to be transmitted through a portion of at least one of the pulp chamber or root canal in said tooth;
   first detector means for receiving at least part of said transmitted light and for producing an electrical output signal which is indicative of the degree of absorption of said light due to blood within said portion of said tooth; and
   second detector means for detecting the presence of an alternating current component of said output signal which is indicative of the presence of said pulse.

11. An apparatus for non-invasively determining the vitality of a tooth, said apparatus comprising:
   means for detecting an interchange of arterial and venous blood in at least one of the pulp chamber or root canal in said tooth; and
   means for indicating that the tooth is vital in the event said interchange is detected, and for indicating that the tooth is non-vital in the event said interchange is not detected.

12. The apparatus of claim 11, wherein said means for detecting said interchange comprises a photoelectric sensor, and wherein said sensor comprises:
light source means for providing light to be transmitted through a portion of at least one of the pulp chamber or root canal in said tooth;
first detector means for receiving at least part of said transmitted light and for producing an electrical output signal which is indicative of the degree of absorption of said light due to both the arterial and venous blood within said portion of said tooth; and
second detector means detecting a variation in said output signal which is indicative of said interchange.

13. The apparatus of claim 12, wherein said light from said light source means comprises light of first and second wavelengths, said first wavelength being a wavelength for which hemoglobin and hemoglobin oxide in a patient's blood each have approximately the same light absorption coefficient, and said second wavelength being a wavelength for which said hemoglobin and hemoglobin oxide have differing light absorption coefficients.

14. The apparatus of claim 13, wherein said first wavelength is in the infrared region of the light spectrum, and said second wavelength is in the visible region of the light spectrum.

15. A method for diagnosing the vitality of a patient's tooth, said method comprising the steps of:
non-invasively measuring the oxygen saturation level of blood contained in at least one of the pulp chamber or root canal of said patient's tooth;
comparing said oxygen saturation level to a predetermined criteria which comprises a first set of oxygen saturation values representing a vital tooth, and a second set of oxygen saturation values which represent a non-vital tooth; and
determining the vitality of said patient's tooth based on said comparison step, wherein said first set of oxygen saturation values comprises the values of 85 to 100 percent, and said second set comprises the values of 0 to 84 percent.

16. A method for diagnosing the vitality of a patient's tooth, said method comprising the steps of:
non-invasively measuring the oxygen saturation level of blood contained in at least one of the pulp chamber or root canal of said patient's tooth;
comparing said oxygen saturation level to a predetermined criteria which comprises a first set of oxygen saturation values representing a vital tooth, and a second set of oxygen saturation values which represent a non-vital tooth; and
determining the vitality of said patient's tooth based on said comparison step, wherein said predetermined criteria further includes a third set of oxygen saturation values which represent various pathological stages of said tooth between vital and non-vital.

17. The method of claim 16, wherein said step of measuring said oxygen saturation comprises the steps of:
transmitting first and second wavelengths of light through at least a portion of said at least one of the pulp chamber or root canal contained within said patient's tooth;
detecting the relative intensities of said first and second wavelengths of light after having been transmitted through said portion of said patient's tooth;
comparing the relative intensities of said detected first and second wavelengths of light in order to arrive at said oxygen saturation measurement.

18. The method of claim 16, further comprising the step of calibrating said oxygen saturation measurement for known error prior to performing said step of comparing said measurement to said predetermined criteria.

19. A method for determining the vitality of a tooth, said method comprising the steps of:
non-invasively testing for the presence of a pulse in at least one of the pulp chamber or root canal in said tooth; and
determining said tooth to be vital in the event said pulse is detected and to be non-vital in the event said pulse is not detected.

20. The method of claim 19, wherein said step of testing for the presence of a pulse comprises the steps of:
transmitting light through a portion of said at least one of the pulp chamber or root canal in said tooth;
receiving at least part of said transmitted light and producing an electrical output signal which is indicative of the degree of absorption of said light due to blood within said portion of said tooth; and
detecting the presence of an alternating current component of said output signal which is indicative of the presence of said pulse.

21. A method for determining the vitality of a tooth, said method comprising the steps of:
non-invasively testing for an interchange of arterial and venous blood in at least one of the pulp chamber or root canal in said tooth; and
determining that the tooth is vital in the event said interchange is detected, and that the tooth is non-vital in the event said interchange is not detected.

22. The method of claim 21, wherein said step for testing for said interchange comprises the steps of:
transmitting light through a portion of said at least one of the pulp chamber or root canal in said tooth;
receiving at least part of said transmitted light and producing an electrical output signal which is indicative of the degree of absorption of said light due to both the arterial and venous blood within said portion of said tooth; and
detecting a variation in said output signal which is indicative of said interchange.

23. A photoelectric sensor for use in the non-invasive diagnosis of tooth vitality, said sensor comprising:
light source means for providing light to be transmitted through at least a portion of a tooth;
detector means for receiving at least part of said transmitted light and for providing an output signal indicative of the amount of said light absorbed by the blood within said tooth;
a sensor body for maintaining said light source and detector means in fixed relation to said tooth;
said light source means and said detector means being capable of being fixedly positioned below a patient's gum line about the root section of said tooth, and
wherein said light source means comprises a first and second light source and said detector means comprises a first and second detector, said first light source and first detector being positioned on said sensor body such that when engaged to said tooth, a first source-to-detector path through the crown section of said tooth is formed, and said second light source and second detector being positioned on said sensor body such that when engaged to said tooth, a second source-to-detector path through the root section of said tooth is formed.

* * * * *